United States Patent [19]

Rivier et al.

[11] 4,224,171

[45] Sep. 23, 1980

[54] NOVEL LUBRICANT ADDITIVES CONTAINING PHOSPHORUS AND NITROGEN AND LUBRICANT COMPOSITIONS CONTAINING THEM

[75] Inventors: Georges Rivier, Bron; Gerard Forat, Lyons, both of France

[73] Assignee: Orogil, Couroevoie, France

[21] Appl. No.: 953,884

[22] Filed: Oct. 23, 1978

[30] Foreign Application Priority Data

Nov. 2, 1977 [FR] France .................... 77 32857

[51] Int. Cl.$^2$ .............................................. C10M 1/48
[52] U.S. Cl. ................................. 252/46.7; 252/49.6; 252/49.9; 260/938
[58] Field of Search .................... 252/46.7, 49.9, 49.6; 260/938

[56] References Cited

U.S. PATENT DOCUMENTS

| | | | |
|---|---|---|---|
| 2,566,288 | 8/1951 | Hook et al. | 252/46.7 X |
| 2,733,207 | 1/1956 | Otto | 252/46.7 X |
| 3,117,150 | 1/1964 | Kerschner et al. | 252/46.7 X |
| 3,328,495 | 6/1967 | Anders et al. | 252/46.7 X |
| 3,725,278 | 4/1973 | Hunger | 252/46.7 |
| 3,794,699 | 2/1974 | Freenor | 260/938 |
| 4,029,679 | 6/1977 | Kötzsch et al. | 260/938 |

OTHER PUBLICATIONS

Levchenko et al., "Esters of Isothiocyanato Phosphoric and Isothiocyanatothiophosphoric Acids", Chem. Ab., vol. 51, 5719e.

Bliznyuk et al., "Substituted Thioureidotrithiophosphates", Chem. Abstracts, vol. 68, 114243r.

Matyusha et al., "Isocyanate Derivatives of Phosphoristhio Acids", Chem. Abstracts, vol. 75, 76309b.

*Primary Examiner*—Andrew Metz

[57] ABSTRACT

Novel lubricant additives containing phosphorus and nitrogen and novel lubricant compositions containing between about 0.2 and 10 percent by weight of said additives are provided. The novel lubricant compositions possess improved wear-resistance and improved properties under extreme pressure.

11 Claims, No Drawings

NOVEL LUBRICANT ADDITIVES CONTAINING PHOSPHORUS AND NITROGEN AND LUBRICANT COMPOSITIONS CONTAINING THEM

BACKGROUND OF THE INVENTION

The present invention relates to novel lubricant additives containing phosphorus and nitrogen and novel lubricant compositions containing them which have improved extreme-pressure and anti-wear properties.

A number of additives containing, in particular, phosphorus and nitrogen which make it possible to improve the mechanical properties of lubricating oils are available on the market; among them, mention may be made of the family of the phosphoramidates, such as those described in U.S. Pat. No. 3,810,838.

As a result of the present invention, new lubricant compositions have been found of even better performance characteristics.

It is, accordingly, an object of the present invention to provide novel lubricants and lubricant additives which provide improved properties.

It is a further object of the present invention to provide novel lubricant additives which contain both phosphorus and nitrogen.

It is also an object of the present invention to provide novel lubricant compositions which have excellent properties at extreme pressure conditions and which resist wear when used to lubricate metals.

Other objects of the invention will be apparent to those skilled in the art from the present disclosure.

GENERAL DESCRIPTION OF THE INVENTION

The novel lubricant additives which form an object of the invention contain both phosphorus and nitrogen. They comprise a derivative of a compound selected from among the isocyanates and isothiocyanates of formula (I):

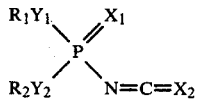

with a nitrogen-containing compound having at least one

radical. In the compound of formula (I), above, $Y_1$, $Y_2$, $X_1$ and $X_2$ are similar or different and represent an oxygen or sulfur atom, and $R_1$ and $R_2$ are similar or different and represent a hydrocarbon group.

Preferably, $R_1$ and $R_2$ are similar or different and represent an alkyl radical of $C_3-C_{20}$, optionally branched, and preferably $C_4-C_{12}$; an alkenyl radical of $C_3-C_{24}$, optionally branched, and preferably $C_3-C_{18}$; a phenyl radical; a phenyl radical substituted by at least one alkyl group of $C_1-C_{24}$ and preferably $C_1-C_{12}$, or by a cycloalkyl radical of $C_3-C_{10}$ and preferably $C_5-C_8$.

In the compound containing at least one

radical, the remaining two valences of the nitrogen atom of said nitrogen compound are preferably satisfied by:

hydrogen;

an alkyl radical of $C_1-C_{24}$, and preferably $C_1-C_{18}$, optionally substituted;

an alkenyl radical of $C_3-C_{24}$, and preferably $C_3-C_{18}$;

an alkynyl radical of $C_3-C_{16}$, and preferably $C_3-C_8$;

a cycloalkyl radical of $C_5-C_{12}$, and preferably $C_5-C_9$;

a polycycloalkyl radical of $C_9-C_{18}$;

a phenyl radical, optionally substituted;

a nitrogen heterocyclic radical, optionally substituted, and optionally containing other hetero-elements;

organic radicals which form a nitrogen hetero-cycle, optionally substituted, with the said nitrogen atom and contain possibly other hetero-elements.

Among the nitrogen-containing compounds corresponding to this preferred type, mention may be made of:

ammonia;

the primary or secondary alkyl monoamines of $C_3-C_{12}$, such as butylamine, hexylamine, decylamine, 2-diethylhexylamine, dodecylamine, and dipropylamine;

the $C_3-C_{12}$ hydroxymonoamines, such as ethanolamine, propanolamine, diethanolamine, and dipropanolamine;

the $C_2-C_{12}$ alkyl diamines, such as hexamethylenediamine and ethylene diamine;

the polyamines, such as the polyalkylene amines and tris(3-oxa-6-amino-hexyl)amine;

the alkenylsuccinimides derived from the above-mentioned amines and whose alkenyl radical has more than 30 carbon atoms;

the alkenylamines derived from the above-mentioned amines and whose alkenyl radical has more than 20 carbon atoms;

α-aminopropyl triethoxy silane
cyclohexylamine
aniline
o-aminophenol
m-trifluoromethylaniline
mercaptotrifluoromethylaniline
N(2-butyl-pentyl)N'(phenylene diamine)
3-amino-1,2,3-triazole
2-amino-benzothiazole
2-amino-benzimidazole
5-amino-2-mercapto-1,3,4-thiadiazole
morpholine Among the isocyanates or isothiocyanates satisfying formula (I), included are the products of the following formulae:

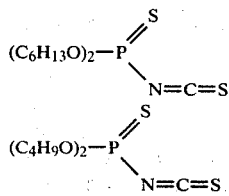

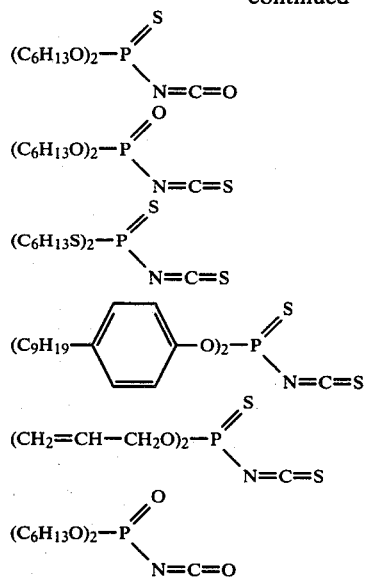

The derivatives of phosphorus and nitrogen which enter into the compositions forming the object of the invention are prepared by the action of an isocyanate or isothiocyanate of formula (I), above, on a nitrogen-containing compound as defined above, in accordance with a ratio of the number of isocyanate or isothiocyanate groups to the number of active $$-\underset{|}{N}-H \text{ groups}$$

of between about 0.5 and 1.25.

The reaction is desirably carried out at a temperature of between about 20° C. and 100° C., and preferably between about 20° C. and 70° C., for about one-half hour to 10 hours, and preferably for between about ¾ hour to 8 hours.

The reaction may optionally be carried out in the presence of an aliphatic solvent (pentane, hexane, etc.) or a benzene solvent (benzene, toluene, etc.), possibly mixed with a polar aprotic solvent (hexamethylphosphorotriamide, N-methyl-pyrolidone, dimethylformamide, dimethylsulfoxide, etc.).

The reaction product is then washed, dried and finally purified.

The lubricating oils to which the lubricant additives of the invention may be added include natural oils of a viscosity of between 20.6 cst (centistokes) and 541 cst at 37.8° C., namely, between 100 and 2500 SUS (Saybolt Universal Viscosity) at 100° F., or synthetic or semi-synthetic bases (synthetic hydrocarbons, esters, polyesters, polyethers) of comparable viscosities.

The quantities of phosphorus and nitrogen containing lubricant additives which can be introduced into the lubricant compositions forming an object of the invention are between about 0.2 and 10 percent by weight of said composition. The particular quantity of additives is a function of the future use of the compositions, namely, as motor, gear-box, or automatic transmission oils, hydraulic fluid, or cutting oil for the mechanical industry.

The compositions which form the object of the invention may also contain anti-oxidant, anti-corrosion, anti-foam, detergent dispersion additives, other extreme-pressure and anti-wear adjuvants, etc., without there resulting herefrom any problem with respect to compatibility or loss in level of performance.

The lubricant compositions which form the object of the invention may be prepared by dissolving the lubricant additive of the invention in the base oil or, when other adjuvants are to be present, by dissolving the additive in the base oil to which said adjuvants have been added or by dissolving the additive in the said adjuvants and adding the base oil.

SPECIFIC DESCRIPTION OF THE INVENTION

In order to disclose more clearly the nature of the present invention, the following examples illustrating the invention are given. It should be understood, however, that this is done solely by way of example and is intended neither to delineate the scope of the invention nor limit the ambit of the appended claims. In the examples which follow, and throughout the specification, the quantities of material are expressed in terms of parts by weight, unless otherwise specified.

EXAMPLE 1

Preparation of N(O,O-dihexylphosphorothiono)-N(hydrogen)-N'(hydrogen)-N'(hexyl)thiourea of the formula

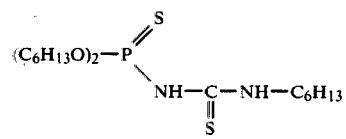

Into a 250 ml. three-necked, round-bottom flask there are introduced 48.5 g. (namely, 0.15 mol) of O,O-dihexylisothiocyanothiophosphate, whereupon 17 g. (i.e., 0.165 mol) of hexylamine are added dropwise over the course of 30 minutes. The temperature is maintained at 24°–25° C. for 45 minutes. A colored homogeneous medium is obtained.

60 ml. of pentane are then added to the medium. The aqueous solution obtained is washed with 50 ml. of distilled water, decanted, and then dried over sodium sulfate.

After distillation of the pentane under vacuum to remove it, there are obtained 58 g. of product, an oil, having the following composition, determined by elementary analysis:

|  | Value Found (%) | Value Calculated (%) |
|---|---|---|
| phosphorus | 7.0 | 7.31 |
| sulfur | 12.9 | 15.09 |
| nitrogen | 6.3 | 6.60 |
| carbon | 54.5 | 53.77 |
| hydrogen | 10 | 9.67 |

The conversion rate with respect to the O,O-dihexylisothiocyanothiophosphate used is 79%.

The yield with respect to the starting material which has reacted is 87%.

The O,O-dihexylisothiocyanothiophosphate used may be prepared in the following manner:

Into a 3 liter three-necked, round-bottom flask there are introduced, with agitation, 361 g. (namely, 3.72 mols) of potassium thiocyanate and 1 liter of dry acetone, whereupon 1015 g. (namely, 3.38 mols) of O,O-dihexylchlorothiophosphate are introduced over the course of 3 hours and 40 minutes, maintaining the temperature at 25°–30° C., a precipitate of KCl is formed.

At the end of the introduction, heating is effected under acetone reflux for two hours. The reaction mixture is allowed to cool, whereupon the acetone solution is decanted and the precipitate which remains is washed with 500 ml. of dry acetone.

The acetone solutions are combined and then distilled under vacuum. In this way there are recovered 771 g. of O,O-dihexylisothiocyanothiophosphate, which is confirmed by elementary analysis:

|  | Value Found (%) | Value Calculated (%) |
| --- | --- | --- |
| phosphorus | 8.9 | 9.60 |
| sulfur | 18.2 | 19.81 |
| nitrogen | 4.0 | 4.33 |

EXAMPLE 2

Preparation of N(O,O-dihexylphosphorothiono)-N(hydrogen)-N'(dipropyl)thiourea of the formula

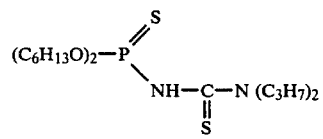

The procedure described in Example 1 is repeated but employing as reactants 32.3 g. (namely, 0.1 mol) of O,O-dihexylisothiocyanothiophosphate and 10 g. (namely, 0.1 mol) of dipropylamine.

There are obtained 40 g. of an oil having the following composition, as determined by elementary analysis:

|  | Value Found (%) | Value Calculated (%) |
| --- | --- | --- |
| phosphorus | 7.3 | 7.31 |
| nitrogen | 6.2 | 6.60 |
| sulfur | 14.9 | 15.09 |
| carbon | 55.3 | 53.8 |
| hydrogen | 9.9 | 9.67 |

The conversion rate is 89%.
The yield is 98%.

EXAMPLE 3

Preparation of N(O,O-dihexylphosphorothiono)-N(hydrogen)-N'(decyl)thiourea of the formula

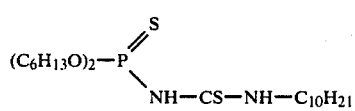

The procedure described in Example 1 is repeated but employing as reactants 32.3 g. (namely, 0.1 mol) of O,O-dihexylisothiocyanothiophosphate and 17.5 g. (namely, 0.1 mol) of decylamine.

There are obtained 47 g. of product the composition of which, determined by elementary analysis is:

|  | Value Found (%) | Value Calculated (%) |
| --- | --- | --- |
| phosphorus | 6.1 | 6.46 |
| nitrogen | 5.8 | 5.83 |
| sulfur | 11.3 | 13.33 |
| carbon | 59.0 | 57.50 |
| hydrogen | 10.5 | 10.21 |

The conversion rate is 87.7%.
The yield is 100%.

EXAMPLE 4

Preparation of N(O,O-dihexlphosphorothiono)-N(hydrogen)-N'(hydrogen)-N'(dodecyl)thiourea of the formula:

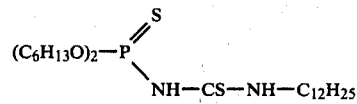

The procedure described in Example 1 is repeated but employing as reactants 32.3 g. (namely, 0.1 mol) of O,O-dihexylisothiocyanothiophosphate and 20.5 g. (namely, 0.11 mol) of dodecylamine solubilized in 70 ml. of pentane.

There are obtained 50 g. of an oil having the composition, determined by elementary analysis, of:

|  | Value Found (%) | Value Calculated (%) |
| --- | --- | --- |
| phosphorus | 5.6 | 6.10 |
| sulfur | 10.5 | 12.60 |
| carbon | 59.8 | 59.05 |
| hydrogen | 10.60 | 10.43 |
| nitrogen | 5.20 | 5.51 |

The conversion rate is 90.2%.
The yield is 100%.

EXAMPLE 5

Preparation of N(O,O-dihexylphosphorothiono)-N(hydrogen)-N'(hydrogen)-N'(cyclohexyl)thiourea of the formula

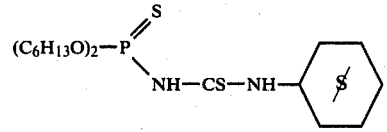

The procedure described in Example 1 is repeated but employing the following reactants: 48.5 g. (namely, 0.15 mol) of O,O-dihexylisothiocyanothiophosphate and 16.5 g. (namely, 0.165 mol) of cyclohexylamine.

There are obtained 62 g. of an oil having a composition, determined by elementary analysis, of:

|  | Value Found (%) | Value Calculated (%) |
| --- | --- | --- |
| phosphorus | 7 | 7.35 |
| sulfur | 13.2 | 15.7 |
| carbon | 54.0 | 54.03 |

|  | Value Found (%) | Value Calculated (%) |
|---|---|---|
| hydrogen | 9.4 | 9.24 |
| nitrogen | 7.1 | 6.64 |

The conversion rate is 92.3%.
The yield is 91.3%.

EXAMPLE 6

Preparation of N(O,O-dihexylphosphorothiono)-N(hydrogen)-N'(hydrogen)-N'(phenyl)thiourea of the formula

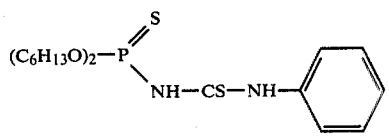

The procedure described in Example 1 is repeated but employing as reactants 32.3 g. (namely, 0.1 mol) of O,O-dihexylisothiocyanothiophosphate and 10.5 g. (namely, 0.11 mol) of aniline.

The product obtained is taken up in 50 ml. of pentane. After washing and distillation of the solvent, there are obtained 41 g. of an oil having a composition, determined by elementary analysis, of:

|  | Value Found (%) | Value Calculated (%) |
|---|---|---|
| phosphorus | 6.6 | 7.45 |
| sulfur | 13.1 | 15.38 |
| nitrogen | 6.5 | 6.73 |
| carbon | 55.5 | 54.81 |
| hydrogen | 8.0 | 7.93 |

The conversion rate is 71.3%.
The yield is 45%.

EXAMPLE 7

Preparation of N(O,O-dihexylphosphorothiono)-N(hydrogen)-N'(hydrogen)-N'(o-hydroxyphenyl)thiourea of the formula

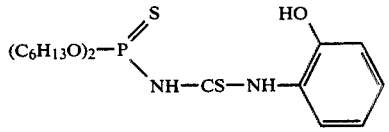

There are introduced into a 250 ml., three-necked, round-bottom flask 32.3 g. (namely, 0.1 mol) of O,O-dihexylisothiocyanothiophosphate, 12 g. (namely, 0.11 mol) of o-aminophenol and 50 ml. of toluene. 5 ml. of hexamethylphosphotriamide are added and heating is effected for 2½ hours at 50° C. Once cooled, the medium is washed with 50 ml. of water and then decanted. The solvent is distilled under vacuum.

There are obtained 42 g. of an oil having a composition, determined by elementary analysis, of:

|  | Value Found (%) | Value Calculated (%) |
|---|---|---|
| phosphorus | 6.8 | 7.18 |

|  | Value Found (%) | Value Calculated (%) |
|---|---|---|
| sulfur | 12.2 | 14.81 |
| nitrogen | 6.7 | 6.48 |
| carbon | 53.2 | 52.78 |
| hydrogen | 7.6 | 7.64 |

The conversion rate is 82%.
The yield is 45.5%.

EXAMPLE 8

Preparation of N(O,O-dihexylphosphorothiono)-N(hydrogen)-N'(hydrogen)-N'(butyl)thiourea of the formula

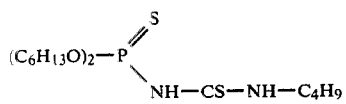

The procedure described in Example 1 is repeated but employing as reactants 32.3 g. (namely, 0.1 mol) of O,O-dihexylisothiocyanothiophosphate and 8 g. (namely, 0.11 mol) of butylamine. The temperature is maintained at 30° C. for 1 hour. Then the product is taken up in 50 ml. of pentane.

There are obtained 38 g. of an oil having a composition, determined by elementary analysis, of:

|  | Value Found (%) | Value Calculated (%) |
|---|---|---|
| phosphorus | 7.3 | 7.83 |
| carbon | 50.5 | 51.51 |
| hydrogen | 9.2 | 9.34 |
| sulfur | 15.0 | 16.16 |
| nitrogen | 6.7 | 7.07 |

The conversion rate is 81%.
The yield is 100%.

EXAMPLE 9

Preparation of N(O,O-dihexylphosphorothiono-N(hydrogen)-N'(hydrogen)-N'(2-ethyl hexyl)thiourea of the formula

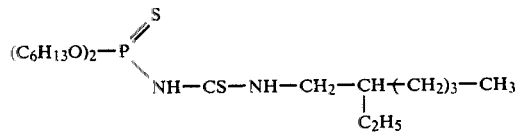

The procedure described in Example 8 is repeated but employing as reactants 32.3 g. (namely, 0.1 mol) of O,O-dihexylisothiocyanothiophosphate and 14.2 g. (namely, 0.11 mol) of 2-ethyl hexylamine.

There are obtained 44 g. of a viscous product having a composition, determined by elementary analysis, of:

|  | Value Found (%) | Value Calculated (%) |
|---|---|---|
| phosphorus | 6.5 | 6.86 |
| carbon | 54.5 | 55.75 |
| hydrogen | 9.8 | 9.95 |
| nitrogen | 5.8 | 6.19 |

| | Value Found (%) | Value Calculated (%) |
|---|---|---|
| sulfur | 13.2 | 14.16 |

The conversion rate is 85%.
The yield is 100%.

EXAMPLE 10

Preparation of N(O,O-dihexylphosphorothiono)-N(hydrogen)-N'(hydrogen)-N'(1,2,3-triazyl-5)thiourea of the formula

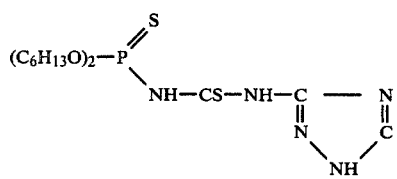

48.5 g. (namely, 0.15 mol) of O,O-dihexylisothiocyanothiophosphate, 14 g. of 3-amino-1,2,3-triazol and 30 ml. of pentane are introduced into a 250 ml. round-bottom flask. This mixture is heated at 50° C. whereupon 30 ml. of hexamethylphosphotriamide are added. The operation requires 7½ hours. After cooling, the mixture is washed with two portions of 60 ml. of water, then decanted and the solvent is eliminated by vacuum distillation.

There are obtained 59 g. of product of a composition, determined by elementary analysis, of:

| | Value Found (%) | Value Calculated (%) |
|---|---|---|
| phosphorus | 8.6 | 7.62 |
| carbon | 44.6 | 44.23 |
| hydrogen | 7.9 | 7.37 |
| sulfur | 13.6 | 15.72 |
| nitrogen | 13.7 | 17.20 |

The conversion rate is 73%.
The yield is 100%.

EXAMPLE 11

Preparation of N(O,O-dihexylphosphorothiono)-N(hydrogen)-N'(hydrogen)-N'(2-benzothiazyl)thiourea of the formula

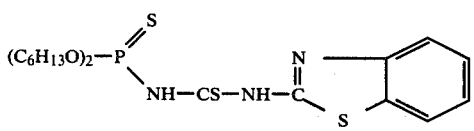

The operation described in Example 13 is repeated but employing as reactants 39 g. (namely, 0.12 mol) of O,O-dihexylisothiocyanothiophosphate, 20 g. (namely, 0.132 mol) of 2-amino benzothiazole, and 50 ml. of hexamethylphosphotriamide, in 100 ml. of toluene. The reaction proceeds for 2½ hours at a temperature of 50° C.

There are obtained 58 g. of a product of a composition, determined by elementary analysis, of:

| | Value Found (%) | Value Calculated (%) |
|---|---|---|
| carbon | 50.5 | 50.74 |
| hydrogen | 7.0 | 6.77 |
| sulfur | 19.7 | 20.30 |
| phosphorus | 7.0 | 6.55 |
| nitrogen | 9 | 8.88 |

The conversion rate is 80.7%.
The yield is 91.4%.

EXAMPLE 12

Preparation of N(O,O-dihexylphosphorothiono-N(hydrogen)-N'(1,3,4-mercaptothiadiazole)thiourea of the formula

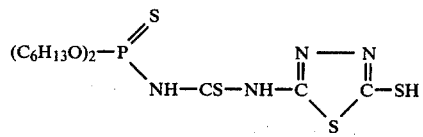

The procedure described in Example 10 is repeated with 32.3 g. (namely, 0.1 mol) of O,O-dihexylisothiocyanothiophosphate, 14.6 g. (namely, 0.11 mol) of 5-amino 2-mercapto-1,3,4-thiadiazole, 50 ml. of toluene and 50 ml. of hexamethylphosphotriamide for 1½ hours at 65° C.

There are obtained 44 g. of product having a composition, determined by elementary analysis, of:

| | Value Found (%) | Value Calculated (%) |
|---|---|---|
| phosphorus | 7.40 | 6.8 |
| nitrogen | 11.7 | 12.28 |
| sulfur | 26.8 | 28.07 |
| carbon | 40.2 | 39.47 |
| hydrogen | 6.5 | 6.36 |

The conversion rate is 7.8%.
The yield is 91.2%.

EXAMPLE 13

Preparation of N(O,O-dihexylphosphorothiono)-N(hydrogen)-N'(hydrogen)-N'(benzimidazolyl)thiourea of the formula

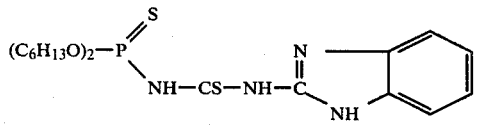

The procedure described in Example 10 is repeated but employing 32.3 g. (namely, 0.10 mol) of O,O-dihexylisothiocyanothiophosphate, 14.6 g. (namely, 0.11 mol) of 2-amino benzimidazole, 50 ml. of toluene and 50 ml. of hexamethylphosphorotriamide for 3 hours at 50° C.

There are obtained 47 g. of product having a composition, determined by elementary analysis, of:

| | Value Found (%) | Value Calculated (%) |
|---|---|---|
| phosphorus | 7.1 | 6.80 |
| nitrogen | 11.8 | 12.28 |

| | Value Found (%) | Value Calculated (%) |
|---|---|---|
| sulfur | 13.7 | 14.04 |
| carbon | 52.0 | 52.63 |
| hydrogen | 7.1 | 7.24 |

The conversion rate is 38%.
The yield is 77%.

EXAMPLE 14

Preparation of N(O,O-dihexylphosphorothiono)-N(hydrogen)-N'(morpholinyl)thiourea of the formula

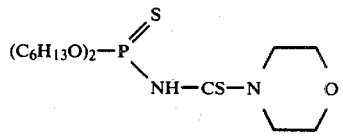

The procedure described in Example 10 is repeated but employing 32.3 g. (namely, 0.10 mol) of O,O-dihexylisothiocyanothiophosphate, 9.6 g. (namely, 0.11 mol) of morpholine, 50 ml. of toluene and 50 ml. of hexamethylphosphorotriamide for 3 hours at 50° C.

There are obtained 38 g. of product having a composition, determined by elementary analysis, of:

| | Value Found (%) | Value Calculated (%) |
|---|---|---|
| phosphorus | 8.0 | 7.56 |
| nitrogen | 6.5 | 6.83 |
| sulfur | 15.2 | 15.61 |
| carbon | 49.5 | 49.76 |
| hydrogen | 8.4 | 8.54 |

The conversion rate is 45%.
The yield is 80%.

EXAMPLE 15

Preparation of N(O,O-dihexylphosphorothiono)-N(hydrogen)-N'(hydrogen)-N'(3-trifluoromethyl phenyl)thiourea of the formula

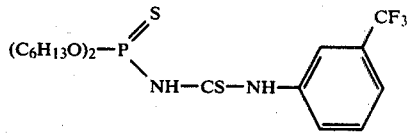

The procedure described in Example 1 is repeated but employing 32.3 g. (namely, 0.10 mol) of O,O-dihexylisothiocyanothiophosphate, 16.25 g. (0.11 mol) of m-trifluoromethylaniline, and 60 ml. of pentane for 1 hour at 28° C.

There are obtained 47 g. of product having a composition, determined by elementary analysis, of:

| | Value Found (%) | Value Calculated (%) |
|---|---|---|
| phosphorus | 6.1 | 6.40 |
| sulfur | 12.7 | 13.22 |
| nitrogen | 5.1 | 5.79 |
| carbon | 50.2 | 49.59 |

| | Value Found (%) | Value Calculated (%) |
|---|---|---|
| hydrogen | 6.9 | 6.61 |
| fluorine | 10.9 | 11.78 |

The conversion rate is 75%.
The yield is 72%.

EXAMPLE 16

Preparation of N(O,O-dihexylphosphorothiono)-N(hydrogen)-N'(mercaptotrifluoromethylphenyl)thiourea of the formula

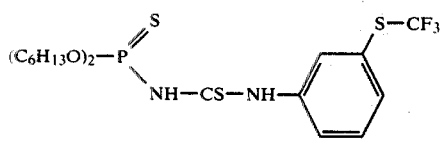

The procedure described in Example 1 is repeated but employing 32.3 g. (namely, 0.1 mol) of O,O-dihexylisothiocyanothiophosphate, 21.2 g. (namely, 0.11 mol) of mercaptotrifluoromethylaniline, and 60 ml. of pentane, for 2 hours at 35° C.

There are obtained 46 g. of product having a composition, determined by elementary analysis, of:

| | Value Found (%) | Value Calculated (%) |
|---|---|---|
| phosphorus | 5.8 | 6.00 |
| sulfur | 17.9 | 18.60 |
| nitrogen | 5.0 | 5.43 |
| carbon | 46.6 | 46.51 |
| hydrogen | 6.3 | 6.20 |
| fluorine | 10.8 | 11.05 |

EXAMPLE 17

Preparation of N(O,O-dihexylphosphorothiono)-N(hydrogen)-N'(hydrogen)-N'(triethoxysilylpropyl)thiourea of the formula

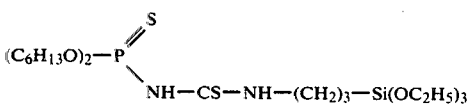

The procedure described in Example 1 is repeated but employing 32.3 g. (namely, 0.1 mol) of O,O-dihexylisothiocyanothiophosphate, 24.2 g. (namely, 0.11 mol) of γ aminopropyltriethoxysilane, and 50 ml. of toluene, for 1½ hours at 35° C.

There are obtained 48 g. of product having a composition, determined by elementary analysis, of:

| | Value Found (%) | Value Calculated (%) |
|---|---|---|
| phosphorus | 5.6 | 5.70 |
| sulfur | 11.5 | 11.76 |
| nitrogen | 4.8 | 5.14 |
| carbon | 49.3 | 48.53 |
| hydrogen | 9.3 | 9.01 |

| | Value Found (%) | Value Calculated (%) |
|---|---|---|
| silicon | 4.90 | 5.15 |

The conversion rate is 100%.
The yield is 100%.

EXAMPLE 18

Preparation of tris[[3(O,O-dihexylphosphorothiono)ureido]₆3-oxa hexyl]amine, of the formula

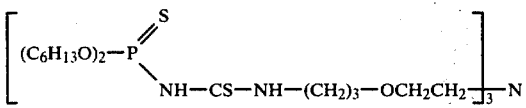

The procedure described in Example 1 is repeated but employing 48 g. (namely, 0.15 mol) of O,O-dihexylisothiocyanothiophosphate, 17.6 g. (namely, 0.055 mol) of tris(6-amino-3-oxa-hexyl)amine, and 70 ml. of toluene, for 2 hours at 50° C.

There are obtained 59 g. of product having a composition, determined by elementary analysis, of:

| | Value Found (%) | Value Calculated (%) |
|---|---|---|
| phosphorus | 6.8 | 7.21 |
| sulfur | 13.7 | 14.9 |
| nitrogen | 6.9 | 7.60 |
| carbon | 51.3 | 50.27 |
| hydrogen | 8.9 | 8.84 |

The conversion rate is 100%.
The yield is 100%.

EXAMPLE 19

Preparation of N(O,O-dihexylphosphorothiono)-N(hydrogen)-N'(p-phenylanilinophenyl)-N'(butyl-2-n-pentyl)thiourea of the formula

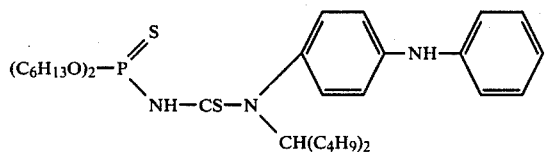

The procedure described in Example 1 is repeated but employing 32.3 g. (namely, 0.10 mol) of O,O-dihexylisothiocyanothiophosphate, 34 g. (namely, 0.11 mol) of N(butyl-2-n-pentyl)N'-phenylene diamine, and 60 ml. of toluene, for 2½ hours at 45° C.

There are obtained 60 g. of product having a composition, determined by elementary analysis, of:

| | Value Found (%) | Value Calculated (%) |
|---|---|---|
| phosphorus | 4.1 | 4.90 |
| sulfur | 9.6 | 10.11 |
| nitrogen | 7.1 | 6.64 |
| carbon | 65.3 | 64.45 |

| | Value Found (%) | Value Calculated (%) |
|---|---|---|
| hydrogen | 8.7 | 8.85 |

The conversion rate is 100%.
The yield is 100%.

EXAMPLE 20

Preparation of bis[N(O,O-dihexylphosphorothiono)-N(hydrogen)-N'(hydrogen)thiourea]hexylene of the formula

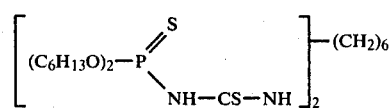

The procedure described in Example 1 is repeated but employing 51.6 g. (namely, 0.16 mol) of O,O-dihexylisothiocyanothiophosphate, 10.2 g. (namely, 0.088 mol) of hexamethylene diamine, and 40 ml. of toluene, for 1 hour at 27° C.

There are obtained 56 g. of product having a composition, determined by elementary analysis, of:

| | Value Found (%) | Value Calculated (%) |
|---|---|---|
| phosphorus | 7.7 | 8.14 |
| sulfur | 16.1 | 16.80 |
| nitrogen | 6.9 | 7.35 |
| carbon | 51.0 | 50.39 |
| hydrogen | 8.9 | 8.92 |

The conversion rate is 98%.
The yield is 86%.

EXAMPLE 21

Preparation of mixtures of tris(O,O-dihexylphosphorothionothiocarbamyl)-1-(polyisobutenylsuccinimido)3,6,9,12-tetraza dodecanes Into a 250 ml. three-necked, round-bottom flask there are introduced 24.5 g. (0.076 mol) of O,O-dihexylisothiocyanothiophosphate and 84.5 g. (namely, 0.076 gram atoms of active nitrogen) of a monopolyisobutenylsuccinimide containing 3.10% nitrogen, including 1.26% active nitrogen, coming from the reaction of tetraethylene pentamine and a polyisobutenylsuccinic anhydride of an acid number equal to 74 obtained by condensation of maleic anhydride on a polyisobutene of a number average molecular weight of 1000. The mixture is heated for 2½ hours at 50° C. There are obtained 87 g. of a product of a composition, determined by elementary analysis, of:

| | Value Found (%) |
|---|---|
| phosphorus | 2.21 |
| sulfur | 4.48 |
| total nitrogen | 2.46 |

EXAMPLE 22

Preparation of bis 3-6(O,O-dihexylphosphorothionothiocarbamyl)bis-1-8(polyisobutylsuccinimido)-3-6-diazo octane Into a 250 ml. three-necked, round-bottom flask there are introduced 7 g. (namely, 0.0217 mol) of O,O-dihexylisothiocyanothiophosphate and 55 g. (namely, 0.0217 gram atoms of active nitrogen) of a bis-polyisobutenyl-succinimide containing 1.2% nitrogen including 0.6% active nitrogen, obtained from the reaction of triethylene tetramine and a polyisobutenyl succinic anhydride of an acid number equal to 74, obtained by condensation of maleic anhydride on a polyisobutene of number average molecular weight of 1000. The mixture is heated for 2½ hours at 45° C.

There are obtained 62 g. of product of a composition, determined by elementary analysis, of:

|  | Value Found (%) |
|---|---|
| phosphorus | 1.12 |
| sulfur | 2.50 |
| nitrogen | 1.82 |

EXAMPLE 23

Preparation of N(O,O-dihexylphosphoro)-N(hydrogen)-N'(dipropyl)-thiourea of the formula:

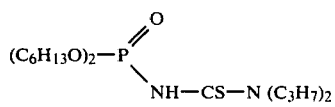

By a procedure equivalent to that described in Example 1, 15.35 g. (namely, 0.05 mol) of O,O-dihexylisothiocyanophosphate, and 5.05 g. (namely, 0.05 mol) of dipropylamine are contacted for 4 hours at room temperature.

There are obtained 21 g. of product of a composition, determined by elementary analysis, of:

|  | Value Found (%) | Value Calculated (%) |
|---|---|---|
| phosphorus | 7.4 | 7.60 |
| sulfur | 7.2 | 7.84 |
| nitrogen | 6.1 | 6.86 |
| carbon | 55.2 | 55.88 |
| hydrogen | 9.8 | 10.05 |

The conversion rate is 92%.
The yield is 100%.

The O,O-dihexylisothiocyanophosphate can be obtained under conditions equivalent to those described in Example 1 so as to obtain O,O-dihexylisothiocyanothiophosphate from potassium thiocyanate and O,O-dihexylchlorophosphate. The composition of the product obtained, determined by elementary analysis, is:

|  | Value Found (%) | Value Calculated (%) |
|---|---|---|
| phosphorus | 9.8 | 10.10 |
| sulfur | 10 | 10.42 |
| nitrogen | 4.10 | 4.56 |

|  | Value Found (%) | Value Calculated (%) |
|---|---|---|
| carbon | 50.60 | 50.81 |
| hydrogen | 8.35 | 8.47 |

EXAMPLE 24

Preparation of N(O,O-dihexylphosphoro)-N(hydrogen)-N'(hydrogen)-N'(dodecyl)thiourea of the formula

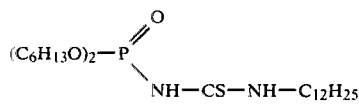

In accordance with a procedure equivalent to that described in Example 4, above, 30.7 g. (namely, 0.10 mol) of O,O-dihexylisothiocyanophosphate and 20.5 g. (namely, 0.11 mol) of n-dodecylamine are contacted.

There are obtained 47 g. of product of a composition, determined by elementary analysis, of:

|  | Value Found (%) | Value Calculated (%) |
|---|---|---|
| phosphorus | 6.15 | 6.3 |
| sulfur | 5.3 | 6.5 |
| nitrogen | 5.3 | 5.69 |
| carbon | 59.9 | 60.98 |
| hydrogen | 10.5 | 10.77 |

The conversion rate is 93.5%.
The yield is 98%.

EXAMPLE 25

Preparation of N(O,O-dihexylphosphoro)-N(hydrogen)-N'(hydrogen)-N'(triethoxysilylpropyl)thiourea of the formula

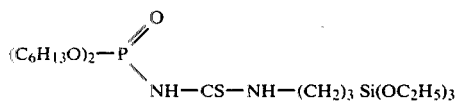

In accordance with a method of operation equivalent to that described in Example 16, above, 30.7 g. (namely, 0.10 mol) of O,O-dihexylisothiocyanophosphate and 24.2 g. (namely, 0.11 mol) of γaminopropyltriethoxysilane are contacted.

There are obtained 52 g. of product of a composition, determined by elementary analysis, of:

|  | Value Found (%) | Value Calculated (%) |
|---|---|---|
| phosphorus | 5.7 | 5.87 |
| sulfur | 5.85 | 6.06 |
| nitrogen | 5.1 | 5.30 |
| carbon | 49.7 | 50.0 |
| hydrogen | 9.1 | 9.28 |
| silicon | 5.2 | 5.30 |

The conversion rate is 86%.
The yield is 92.5%.

EXAMPLE 26

Preparation of
N(S,S-dihexylphosphorothiono)-N(hydrogen)-N'(dipropyl)thiourea of the formula

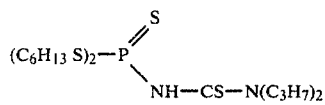

In accordance with a procedure equivalent to that described in Example 1, above, 35.5 g. (0.1 mol) of S,S-dihexylisothiocyanothiophosphate and 10 g. (0.1 mol) of dipropylamine are contacted for ¾ hour at 25° C.

There are obtained 41 g. of product of a component, determined by elementary analysis, of:

|  | Value Found (%) | Value Calculated (%) |
|---|---|---|
| phosphorus | 6.7 | 6.8 |
| sulfur | 27.5 | 28.07 |
| nitrogen | 5.9 | 6.14 |
| carbon | 49.8 | 50.0 |
| hydrogen | 8.75 | 8.99 |

The conversion rate is 79%.
The yield is 84%.

The S,S-dihexylisothiocyanothiophosphate used can be obtained under conditions equivalent to those described in Example 1 so as to obtain the O,O-dihexylisothiocyanothiophosphate from potassium thiocyanate and S,S-dihexylchlorothiophosphate. The composition of the product obtained, determined by elementary analysis, is:

|  | Value Found (%) | Value Calculated (%) |
|---|---|---|
| phosphorus | 8.5 | 8.73 |
| sulfur | 35.5 | 36.06 |
| nitrogen | 3.7 | 3.94 |
| carbon | 43.7 | 43.94 |
| hydrogen | 7.2 | 7.32 |

EXAMPLE 27

Preparation of
N(O,O-diallylphosphorothiono)-N(hydrogen)-N'(dipropyl)thiourea of the formula

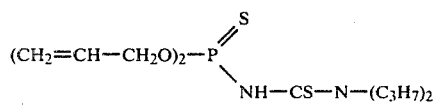

In accordance with a procedure equivalent to that described in Example 1, above, 23.5 g. (0.1 mol) of O,O-diallylisothiocyanothiophosphate and 10 g. (0.1 mol) of dipropylamine are contacted.

There are obtained 30 g. of a product of a composition, determined by elementary analysis, of:

|  | Value Found (%) | Value Calculated (%) |
|---|---|---|
| phosphorus | 9.1 | 9.23 |
| sulfur | 18.7 | 19.05 |
| nitrogen | 8.1 | 8.33 |
| carbon | 46.6 | 46.43 |
| hydrogen | 7.5 | 7.44 |

The conversion rate is 94%.
The yield is 97%.

The O,O-diallylisothiocyanothiophosphate can be obtained under conditions equivalent to those described in Example 1 in order to obtain the O,O-dihexylisothiocyanothiophosphate from potassium thiocyanate and O,O-diallylchlorothiophosphate. The composition of the product obtained, determined by elementary analysis, is:

|  | Value Found (%) | Value Calculated (%) |
|---|---|---|
| phosphorus | 13.0 | 13.19 |
| sulfur | 26.9 | 27.23 |
| nitrogen | 5.7 | 5.96 |
| carbon | 35.7 | 35.74 |
| hydrogen | 4.3 | 4.26 |

EXAMPLE 28

Preparation of
N(O,O-dibutylphosphorothiono)-N(hydrogen)-N'(dipropyl)thiourea of the formula

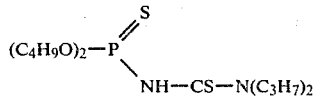

In accordance with a procedure equivalent to that described in Example 1, above, 26.5 g. (0.1 mol) of O,O-dibutylisothiocyanothiophosphate and 10 g. (0.1 mol) of dipropylamine are contacted.

There are obtained 34 g. of a product of a composition, determined by elementary analysis, of:

|  | Value Found (%) | Value Calculated (%) |
|---|---|---|
| phosphorus | 8.3 | 8.42 |
| sulfur | 17.1 | 17.39 |
| nitrogen | 7.4 | 7.61 |
| carbon | 49.1 | 48.91 |
| hydrogen | 9.2 | 8.97 |

The conversion rate is 92%.
The yield is 100%.

The O,O-dibutylisothiocyanothiophosphate used can be obtained under conditions equivalent to those described in Example 1 in order to obtain the O,O-dibutylisothiocyanothiophosphate from potassim thiocyanate and O,O-dibutylchlorophosphate. The composition of the product obtained, determined by elementary analysis, is:

|  | Value Found (%) | Value Calculated (%) |
|---|---|---|
| phosphorus | 11.4 | 11.61 |
| sulfur | 23.7 | 23.97 |
| nitrogen | 5.0 | 5.24 |
| carbon | 40.6 | 40.45 |

| | Value Found (%) | Value Calculated (%) |
|---|---|---|
| hydrogen | 6.8 | 6.74 |

EXAMPLE 29

Preparation of N(O,O-dinonylphenylphosphorothiono)-N(hydrogen)-N'(dipropyl)thiourea of the formula

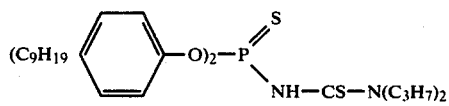

In accordance with a procedure equivalent to that described in Example 1, above, 10.0 g. (0.1 mol) of dipropylamine and 55.9 g. (0.1 mol) of O,O-dinonylphenylisothiocyanothiophosphate are contacted.

There are obtained 62 g. of a product of a composition, determined by elementary analysis, of:

| | Value Found (%) | Value Calculated (%) |
|---|---|---|
| phosphorus | 4.5 | 4.70 |
| sulfur | 9.4 | 9.70 |
| nitrogen | 4.0 | 4.24 |
| carbon | 67.6 | 67.27 |
| hydrogen | 9.4 | 9.24 |

The conversion rate is 90%.
The yield is 98%.

The O,O-dinonylphenylthiocyanothiophosphate used can be obtained under conditions equivalent to those described in Example 1 in order to obtain the O,O-dihexylisothiocyanothiophosphate from potassium thiocyanate and the O,O-dinonylphenylchlorothiophosphate. The composition of the product obtained, determined by elementary analysis, is:

| | Value Found (%) | Value Calculated (%) |
|---|---|---|
| phosphorus | 5.4 | 5.55 |
| sulfur | 11.3 | 11.45 |
| nitrogen | 2.4 | 2.50 |
| carbon | 66.2 | 66.55 |
| hydrogen | 8.3 | 8.23 |

EXAMPLE 30

Preparation of N(O,O-dihexylphosphorothiono)-N(hydrogen)-N'(dipropyl)urea of the formula

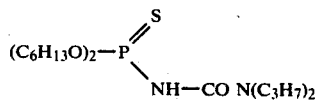

In accordance with a procedure equivalent to that described in Example 1, above, 30.7 g. (0.1 mol) of O,O-dihexylisocyanothiophosphate and 10 g. (0.1 mol) of dipropylamine are contacted.

There are obtained 38 g. of an oil of a composition, determined by elementary analysis, of:

| | Value Found (%) | Value Calculated (%) |
|---|---|---|
| phosphorus | 7.5 | 7.6 |
| nitrogen | 6.7 | 6.86 |
| sulfur | 7.6 | 7.84 |
| carbon | 55.7 | 55.88 |
| hydrogen | 9.9 | 10.05 |

The conversion rate is 95%.
The yield is 98%.

The O,O-dihexylisocyanothiophosphate used can be obtained under conditions equivalent to those described in Example 1 from potassium isocyanate and O,O-dihexylchlorothiophosphate. The composition of the product obtained, determined by elementary analysis, is:

| | Value Found (%) | Value Calculated (%) |
|---|---|---|
| phosphorus | 10.0 | 10.10 |
| nitrogen | 4.4 | 4.56 |
| sulfur | 10.2 | 10.42 |
| carbon | 50.3 | 50.83 |
| hydrogen | 8.4 | 8.47 |

EXAMPLE 31

Preparation of N(O,O-dihexylphosphoro)-N(hydrogen)-N'(dipropyl)urea of the formula

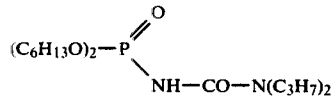

In accordance with a procedure equivalent to that described in Example 1, above, 29.1 g. (0.1 mol) of O,O-dihexylisocyanophosphate and 10 g. (0.1 mol) of dipropylamine are contacted.

There are obtained 37 g. of an oil of a composition, determined by elementary analysis, of:

| | Value Found (%) | Value Calculated (%) |
|---|---|---|
| phosphorus | 7.8 | 7.91 |
| nitrogen | 7.0 | 7.14 |
| carbon | 58.0 | 58.16 |
| hydrogen | 10.4 | 10.46 |

The conversion rate is 94%.
The yield is 96%.

The O,O-dihexylisocyanophosphate used can be obtained under conditions similar to those described in Example 23 from potassium isocyanate and O,O-dihexylchlorophosphate. The composition of the product obtained, determined by elementary analysis, is:

| | Value Found (%) | Value Calculated (%) |
|---|---|---|
| phosphorus | 10.4 | 10.65 |
| nitrogen | 4.6 | 4.82 |
| carbon | 53.4 | 53.61 |

-continued

| | Value Found (%) | Value Calculated (%) |
|---|---|---|
| hydrogen | 8.8 | 8.93 |

EXAMPLE 32

A lubricant composition is prepared by adding to a 10W30 oil an amount of product obtained from one of Examples 1 to 31, corresponding to 0.9% phosphorus by weight.

The mechanical properties of these resulting lubricant compositions are tested on:

(1) Four-ball machine, in accordance with ASTM Standard D 2783-69 T. This test gives the diameter in millimeters of the imprint under a seizing load of 70, 90, 110 and 130 kg., as well as the welding load in kilograms.

(2) Falex machine—this test indicates the wear of the pin (that is to say, of the wear specimen) in mg. at the end of 30 minutes under a pressure of 500 lbs. (271.5 kg.).

The resistance to oxidation of this composition is evaluated by the Mobil oxidation test consisting of oxidizing 33 g. of oil containing the additive, heating to 180° C. for 48 hours in the presence of oxidation catalysts (Pb-Cu) in a flow of air of 13.9 liters per hour, and measuring the increase in viscosity at 210° F. (98.9° C.) of the oxidized oil as compared with new oil.

Comparable tests were carried out on compositions in which the product of one of Examples 1 to 31 is replaced by the same quantity, expressed in % of phosphorus, and one of the following commmercial additives, all containing phosphorus and nitrogen, with the exception of additive G:

additive A: "TLA 202" marketed by Texaco Inc.
additive B: "Improvex 33" marketed by Rhone-Poulenc
additive C: "Ortholeum 535" marketed by Du Pont de Nemours
additive D: "Eca 5215" marketed by Oronite
additive E: "Oloa 259" marketed by Exxon
additive F: "Lubrizol 797" marketed by Lubrizol
additive G: base of a mixture of zinc alkyldithiophosphate, the alkyl radicals of which contain 4 to 6 carbon atoms.

The results of all of these tests are given in Tables 1, 1a, 1b and 1c, respectively, appearing below.

TABLE 1

| | | Mechanical Properties | | | | | | | |
|---|---|---|---|---|---|---|---|---|---|
| | | Before Oxidation | | | | | | After Oxidation | Oxidation |
| | % by | Four-Ball Test | | | | | | Seizure | Increase |
| Products | Weight | Seizure imprint in mm. | | | | Welding | Falex | imprint | in |
| of | of | 70 | 90 | 110 | 130 | load | in | in | Viscosity |
| Examples | Product | kg. | kg. | kg. | kg. | kg. | mm. | mm.-100 kg. | % |
| 1 | 1.42 | — | 0.43 | 0.50 | 0.91 | 300 | 1.9 | 1.9 | 40 |
| 2 | 1.37 | — | 0.48 | 0.49 | 0.90 | 250 | 3.3 | 2.0 | 30 |
| 3 | 1.64 | — | 0.46 | 1.90 | — | 250 | 5.2 | 1.4 | 40 |
| 4 | 1.79 | — | 0.42 | 1.70 | — | 250 | 3.0 | 1.7 | 20 |
| 5 | 1.43 | — | 0.48 | 0.50 | 2.5 | 300 | 2.4 | 1.8 | 20 |
| 6 | 1.52 | — | 0.47 | 0.50 | 2.0 | 300 | 6.0 | 1.8 | 30 |
| 7 | 1.47 | — | 0.47 | 0.52 | 2.5 | 300 | 4.0 | 1.9 | 30 |
| 8 | 1.37 | — | 0.46 | 0.53 | 0.95 | 300 | 1.8 | 1.7 | 30 |
| 9 | 1.54 | — | 0.42 | 1.50 | — | 250 | 3.0 | 1.9 | 40 |
| 10 | 1.16 | — | 0.44 | 1.80 | — | 250 | 3.4 | 1.6 | 30 |

TABLE 1a

| | | Mechanical Properties | | | | | | | |
|---|---|---|---|---|---|---|---|---|---|
| | % by | Before Oxidation | | | | | | After Oxidation Seizure | Oxidation Increase |
| Products | Weight | Seizure imprint in mm. | | | | Welding | Falex | imprint | in |
| of | of | 70 | 90 | 110 | 130 | load | in | in | Viscosity |
| Examples | Product | kg. | kg. | kg. | kg. | kg. | mm. | mm.-100 kg. | % |
| 11 | 1.43 | — | 0.45 | 1.90 | — | 250 | 2.9 | 2.0 | 150 |
| 12 | 1.35 | — | 0.44 | 0.60 | 2.5 | 300 | 0.8 | 1.6 | 50 |
| 13 | 1.41 | — | 0.46 | 1.40 | — | 250 | 4.1 | 2.0 | 150 |
| 14 | 1.25 | — | 0.48 | 1.45 | — | 250 | 3.8 | 2.0 | 120 |
| 15 | 1.64 | — | 0.44 | 0.48 | 0.92 | 300 | 3.6 | 1.7 | 20 |
| 16 | 1.72 | — | 0.45 | 0.49 | 0.91 | 300 | 3.4 | 1.8 | 30 |
| 17 | 1.79 | — | 0.40 | 0.52 | 2.0 | 300 | 3.4 | 1.7 | 30 |
| 18 | 1.47 | — | 0.43 | 0.51 | 1.5 | 300 | 3.7 | 1.4 | 60 |
| 19 | 2.44 | — | 0.49 | 0.43 | 2.5 | 300 | 3.6 | 1.6 | 20 |
| 20 | 1.30 | — | 0.50 | 0.90 | — | 300 | 3.7 | 1.9 | 20 |

TABLE 1b

| Products of Examples | % by Weight of Product | Mechanical Properties | | | | | | After Oxidation Seizure imprint in mm.-100 kg. | Oxidation Increase in Viscosity % |
|---|---|---|---|---|---|---|---|---|---|
| | | Before Oxidation | | | | | | | |
| | | Seizure imprint in mm. | | | | Welding load kg. | Falex in mm. | | |
| | | 70 kg. | 90 kg. | 110 kg. | 130 kg. | | | | |
| 21 | 4.52 | — | 0.45 | 1.50 | — | 250 | 6.5 | 2.0 | 150 |
| 22 | 8.93 | — | 0.47 | 1.80 | — | 250 | 4.1 | 2.0 | 150 |
| 23 | 1.35 | — | 0.43 | 0.49 | 0.93 | 300 | 3.4 | 1.6 | 70 |
| 24 | 1.63 | — | 0.47 | 1.80 | — | 250 | 3.5 | 2.0 | 50 |
| 25 | 1.75 | — | 0.42 | 0.53 | 2.5 | 300 | 3.1 | 1.8 | 100 |
| 26 | 1.49 | — | 0.40 | 0.51 | 0.92 | 300 | 3.2 | 1.7 | 30 |
| 27 | 1.10 | — | 0.49 | 0.55 | 2.4 | 250 | 3.8 | 2.0 | 100 |
| 28 | 1.20 | — | 0.43 | 0.48 | 0.90 | 300 | 3.0 | 1.8 | 30 |
| 29 | 2.22 | — | 0.45 | 0.53 | 0.97 | 250 | 3.2 | 1.9 | 50 |
| 30 | 1.33 | — | 0.47 | 0.50 | 2.5 | 250 | 3.2 | 1.9 | 30 |
| 31 | 1.28 | — | 0.46 | 0.52 | — | 250 | 3.5 | 2.0 | 80 |

TABLE 1c

| Products of Examples | % by Weight of Product | Mechanical Properties | | | | | | After Oxidation Seizure imprint in mm.-100 kg. | Oxidation Increase in Viscosity % |
|---|---|---|---|---|---|---|---|---|---|
| | | Before Oxidation | | | | | | | |
| | | Seizure imprint in mm. | | | | Welding load kg. | Falex in mm. | | |
| | | 70 kg. | 90 kg. | 110 kg. | 130 kg. | | | | |
| A | 10 | 0.41 | 2 | — | — | 200 | 8.2 | — | en masse |
| B | 1.24 | 0.41 | 0.47 | 2.5 | — | 250 | 14.9 | 1.9 | 50 |
| C | 1.47 | — | 2.1 | — | — | 250 | 6.1 | — | en masse |
| D | 3.37 | — | 0.46 | 0.48 | 2.5 | 300 | 9.6 | 1.9 | 50 |
| E | 4.17 | — | 0.41 | 1.9 | — | 250 | 8.1 | 2.4 | 150 |
| F | 4.08 | — | 2.6 | — | — | 200 | 1.0 | 1.8 | 300 |
| G | 1.35 | — | 0.42 | 2.2 | — | 250 | 10.5 | 1.9 | 80 |

It can be seen from Tables 1, 1a, 1b and 1c that the compositions forming the object of the present invention have a very high general performance level with respect to their mechanical properties and retain these performances well despite oxidation. The antioxidant properties are also excellent.

EXAMPLE 33

Lubricant compositions are prepared by adding to a 10W30 oil the product prepared in Example 2, above, in different concentrations.

These compositions are tested in accordance with the methods described in the preceding example. These lubricant compositions are also tested on a Four-ball machine under a load of 150 kg. The results of these tests appear in Table 2, below.

TABLE 2

| % by Weight of Product | Mechanical Properties | | | | | | | After Oxidation Seizure imprint in mm.-100 Kg. | Oxidation Increase in Viscosity |
|---|---|---|---|---|---|---|---|---|---|
| | Before Oxidation | | | | | | | | |
| | Four-Ball Test Seizure imprint in mm. | | | | | Welding load kg. | Falex in mm. | | |
| | 70 kg. | 90 kg. | 110 kg. | 130 kg. | 150 kg. | | | | |
| 0.5 | — | 0.48 | 0.5 | 1.1 | — | 200 | 2.7 | 1.8 | 50 |
| 1.35 | — | 0.48 | 0.49 | 0.9 | 2.5 | 250 | 3.3 | 2 | 30 |
| 2.5 | — | 0.48 | 0.49 | 0.7 | 1.1 | 250 | 3.9 | 1.8 | 30 |
| 4 | — | 0.48 | 0.50 | 0.5 | 0.9 | 250 | 7.3 | 2 | 30 |
| 5 | — | 0.47 | 0.51 | 0.5 | 0.55 | 250 | 10.6 | 1.8 | 30 |

It can be seen that these compositions show an excellent general performance level with respect to their mechanical and antioxidant properties, even with a low concentration of additive.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What is claimed is:

1. A lubricant composition comprising a major proportion of an oil of lubricating viscosity and containing from about 0.2 to 10 percent by weight of a lubricant additive comprising a derivative of a compound selected from the class consisting of isocyanates and isothiocyanates of the formula:

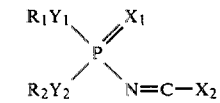

in which formula $Y_1$, $Y_2$, $X_1$ and $X_2$ are members selected from the class consisting of oxygen and sulfur atoms, and $R_1$ and $R_2$ represent hydrocarbon groups; with a nitrogen-containing compound having at least one

radical, wherein the two remaining values of the

radical of said nitrogen compound are satisfied by a member selected from the class consisting of:
- hydrogen;
- an alkyl radical of $C_1-C_{24}$;
- an alkenyl radical of $C_3-C_{24}$;
- an alkynyl radical of $C_3-C_{16}$;
- a cycloalkyl radical of $C_5-C_{12}$;
- a polycycloalkyl radical of $C_9-C_{18}$;
- a phenyl radical;
- a nitrogen-containing heterocyclic radical;
- a nitrogen-containing heterocyclic radical also containing other hetero-elements; and
- organic radicals forming with said nitrogen atom a nitrogen-containing heterocycle.

2. A lubricant composition comprising a major proportion of an oil of lubricating viscosity and containing from about 0.2 to 10 percent by weight of a lubricant additive according to claim 1, wherein $R_1$ and $R_2$ represent members selected from the class consisting of an alkyl radical of $C_3-C_{20}$, an alkenyl radical of $C_3-C_{24}$, a phenyl radical, a phenyl radical substituted by at least one alkyl group of $C_1-C_{24}$, and a phenyl radical substituted by a cycloalkyl radical of $C_3-C_{10}$.

3. A lubricant composition comprising a major proportion of an oil of lubricating viscosity and containing from about 0.2 to 10 percent by weight of a lubricant additive according to claim 1, wherein $R_1$ and $R_2$ represent members selected from the class consisting of an alkyl radical of $C_4-C_{12}$, an alkenyl radical of $C_3-C_{18}$, a phenyl radical, a phenyl radical substituted by at least one alkyl group of $C_1-C_{12}$, and a phenyl radical substituted by a cycloalkyl radical of $C_5-C_8$.

4. A lubricant composition comprising a major proportion of an oil of lubricating viscosity and containing from about 0.2 to 10 percent by weight of a lubricant additive according to claim 2, wherein said alkyl radical and said alkenyl radical are branched.

5. A lubricant composition comprising a major proportion of an oil of lubricating viscosity and containing from about 0.2 to 10 percent by weight of a lubricant additive according to claim 3, wherein said alkyl radical and said alkenyl radical are branched.

6. A lubricant composition comprising a major proportion of an oil of lubricating viscosity and containing from about 0.2 to 10 percent by weight of a lubricant additive according to claim 1, wherein the isocyanate or isothiocyanate is selected from the class consisting of O,O-dihexylisothiocyanothiophosphate, O,O-dibutylisothiocyanothiophosphate, O,O-dinonylphenylisothiocyanothiophosphate, O,O-diallylisothiocyanothiophosphate, O,O-dihexylisocyanothiophosphate, O,O-dihexylisocyanophosphate, S,S-dihexylisothiocyanophosphate and O,O-dihexylisothiocyanophosphate.

7. A lubricant composition comprising a major proportion of an oil of lubricating viscosity and containing from about 0.2 to 10 percent by weight of a lubricant additive according to claim 1, wherein the alkyl radical contains from 1 to 18 carbon atoms, the alkenyl radical contains from 3 to 18 carbon atoms, the alkynyl radical contains from 3 to 8 carbon atoms, and the cycloalkyl radical contains from 5 to 9 carbon atoms.

8. A lubricant composition comprising a major proportion of an oil of lubricating viscosity and containing from about 0.2 to 10 percent by weight of a lubricant additive according to claim 1, wherein the said nitrogen compound is selected from among:
- ammonia;
- $C_3-C_{12}$ alkylmonoamines;
- $C_3-C_{12}$ hydroxymonoamines;
- $C_2-C_{12}$ alkyl diamines;
- a polyalkylene polyamine;
- tris(3-oxa-6-amino-hexyl)amine;
- alkenylsuccinimides derived from polyamines and the alkenyl radical of which has more than 30 carbon atoms;
- alkenyl amines whose alkenyl radical has more than 20 carbon atoms;
- γ-aminopropyltriethoxysilane;
- cyclohexylamine;
- aniline;
- o-aminophenol;
- m-trifluoromethylaniline;
- mercaptotrifluoromethylaniline;
- N(2-butyl pentyl)N'(phenylene diamine);
- 3-amino-1,2,3-triazole;
- 2-amino-benzothiazole;
- 2-aminobenzimidazole;
- 5-amino-2-mercapto-1,3,4-thiadiazole;
- morpholine.

9. A lubricant composition comprising a major proportion of an oil of lubricating viscosity and containing from about 0.2 to 10 percent by weight of a lubricant additive according to claim 1, wherein a derivative is formed by the action between the isocyanate or isothiocyanate and the nitrogen-containing compound at a temperature of between about 20° C. and 100° C. for about one-half to 10 hours with a ratio of number of isocyanate or isothiocyanate groups to number of active

groups of between 0.25 and 1.25.

10. A lubricant composition comprising a major proportion of an oil of lubricating viscosity and containing from about 0.2 to 10 percent by weight of a lubricant additive according to claim 1, wherein two remaining values of the

radical of said nitrogen compound are satisfied by a member selected from the class consisting of:
- hydrogen;
- an alkyl radical of $C_1-C_{24}$;

an alkenyl radical of $C_3$–$C_{24}$;
an alkylnyl radical of $C_3$–$C_{16}$;
a cycloalkyl radical of $C_5$–$C_{12}$;
a polycycloalkyl radical of $C_9$–$C_{18}$;
a phenyl radical.

11. A lubricant composition comprising a major proportion of an oil of lubricating viscosity and containing from about 0.2 to 10 percent by weight of a lubricant additive according to claim 1, wherein the said nitrogen compound is selected from among:

ammonia;
$C_3$–$C_{12}$ alkylmonoamines;
$C_3$–$C_{12}$ hydroxymonoamines;
$C_2$–$C_{12}$ alkyl diamines;
polyalkyl polyamines;
tris(3-oxa-6-amino-hexyl)amine;
alkenyl amines whose alkenyl radical has more than 20 carbon atoms;
cyclohexylamine;
aniline;
o-aminophenol;
m-trifluoromethylaniline;
mercaptotrifluoromethylaniline;
N(2-butyl pentyl)N'(phenylene diamine).

UNITED STATES PATENT AND TRADEMARK OFFICE
CERTIFICATE OF CORRECTION

PATENT NO. : 4,224,171
DATED : September 23, 1980
INVENTOR(S) : Georges Rivier et al.

It is certified that error appears in the above-identified patent and that said Letters Patent are hereby corrected as shown below:

Column 6, line 17, delete "N(O,O-dihexlphosphorothiono)" and replace with -- N(O,O-dihexylphosphorothiono) --.

Column 23, Table 1c, second column of table, fourth number down, delete "3.37" and replace with -- 3.73 --.

Signed and Sealed this

Twenty-third Day of December 1980

[SEAL]

Attest:

SIDNEY A. DIAMOND

Attesting Officer

Commissioner of Patents and Trademarks